US008846084B2

(12) United States Patent
Mandaogade et al.

(10) Patent No.: US 8,846,084 B2
(45) Date of Patent: Sep. 30, 2014

(54) CONTROLLED RELEASE COMPOSITIONS CONTAINING ZOLPIDEM

(75) Inventors: Prashant Manohar Mandaogade, Amravati (IN); Venkatesh Madhavacharya Joshi, Raichur (IN); Girish Kumar Jain, Delhi (IN)

(73) Assignee: Wockhardt Ltd, Bandra-Kurla Complex, Bandra East, Mumbai (IN)

( * ) Notice: Subject to any disclaimer, the term of this patent is extended or adjusted under 35 U.S.C. 154(b) by 1334 days.

(21) Appl. No.: 11/991,361

(22) PCT Filed: Dec. 15, 2006

(86) PCT No.: PCT/IB2006/003624
§ 371 (c)(1),
(2), (4) Date: Sep. 16, 2008

(87) PCT Pub. No.: WO2007/069061
PCT Pub. Date: Jun. 21, 2007

(65) Prior Publication Data
US 2009/0156631 A1    Jun. 18, 2009

(30) Foreign Application Priority Data

Dec. 16, 2005  (IN) .......................... 1586/MUM/05
Dec. 16, 2005  (IN) .......................... 1588/MUM/05
Jan. 12, 2006  (IN) .......................... 47/MUM/2006

(51) Int. Cl.
*A61K 9/22*    (2006.01)
*A61K 9/26*    (2006.01)
*A61K 31/44*   (2006.01)
*A61K 9/20*    (2006.01)
*A61K 9/50*    (2006.01)
*A61K 9/24*    (2006.01)

(52) U.S. Cl.
CPC ............. *A61K 9/2013* (2013.01); *A61K 9/5084* (2013.01); *A61K 9/2018* (2013.01); *A61K 9/2054* (2013.01); *A61K 9/209* (2013.01)
USPC .......................... 424/468; 424/470; 514/300

(58) Field of Classification Search
CPC . A61K 9/2013; A61K 9/2018; A61K 9/2054; A61K 9/209; A61K 9/5084; A61K 9/2081; C07D 471/04
USPC .................................. 424/468, 470; 514/300
See application file for complete search history.

(56) References Cited

U.S. PATENT DOCUMENTS

| 6,514,531 | B1 * | 2/2003 | Alaux et al. .................. 424/468 |
| 6,638,535 | B2 * | 10/2003 | Lemmens et al. ............. 424/489 |
| 2004/0258750 | A1 * | 12/2004 | Alaux et al. .................. 424/464 |

* cited by examiner

*Primary Examiner* — Aradhana Sasan
(74) *Attorney, Agent, or Firm* — Bio Intellectual Property Services LLC (Bio IPS); O. (Sam) Zaghmout

(57) ABSTRACT

The present invention relates to controlled release compositions of Zolpidem or pharmaceutically acceptable salts thereof adapted to release Zolpidem over a predetermined time period, according to a monophasic and/or a biphasic profile of dissolution. The present invention also relates to monolithic matrix based formulations of Zolpidem or pharmaceutically acceptable salts thereof.

10 Claims, 3 Drawing Sheets

COMPARATIVE DRUG RELEASE PROFILE

FIGURE 1: COMPARATIVE DRUG RELEASE PROFILE
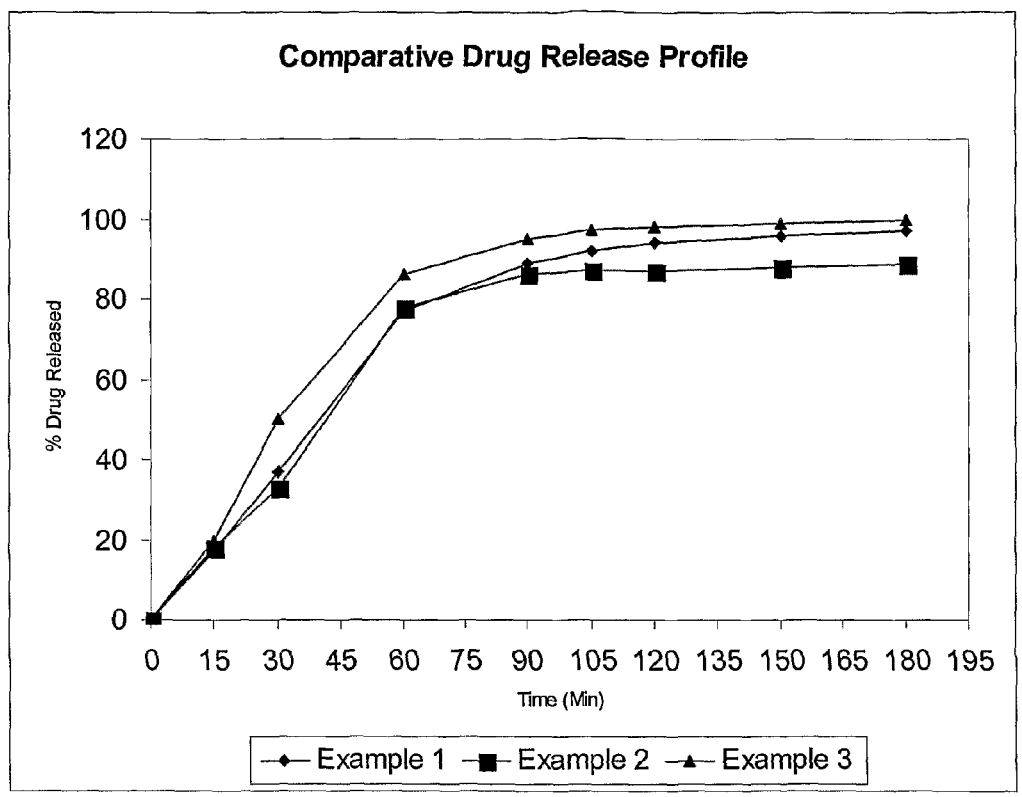

FIGURE 2: COMPARATIVE DRUG RELEASE PROFILE
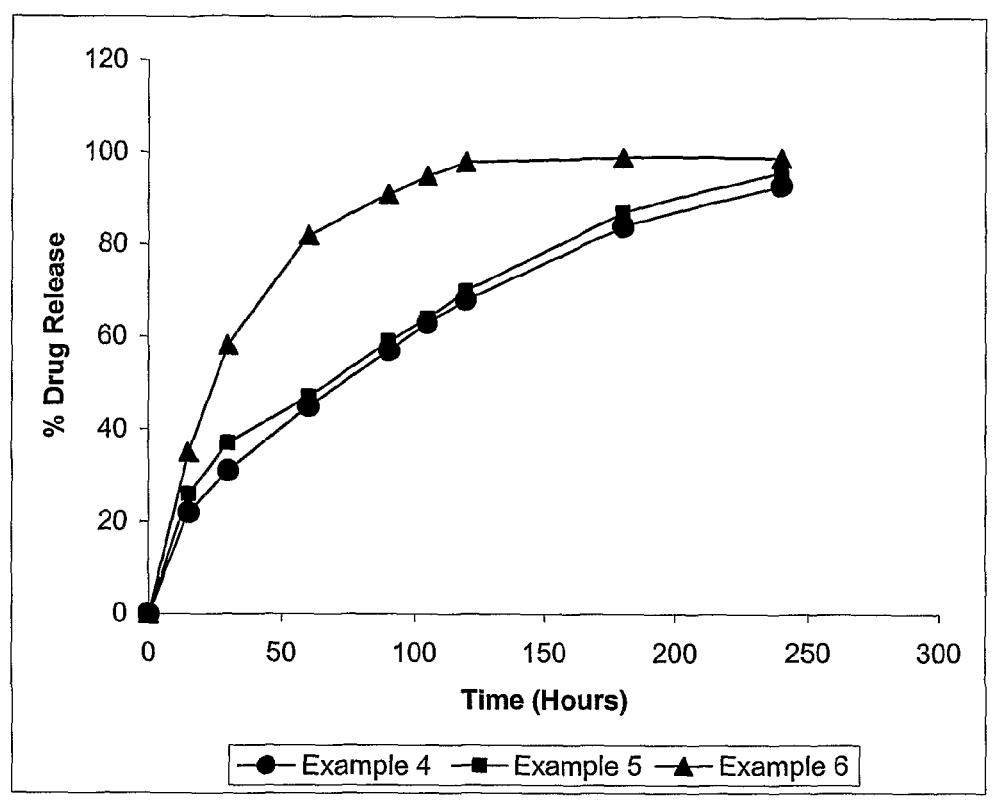

FIGURE 3: COMPARATIVE DRUG RELEASE PROFILE
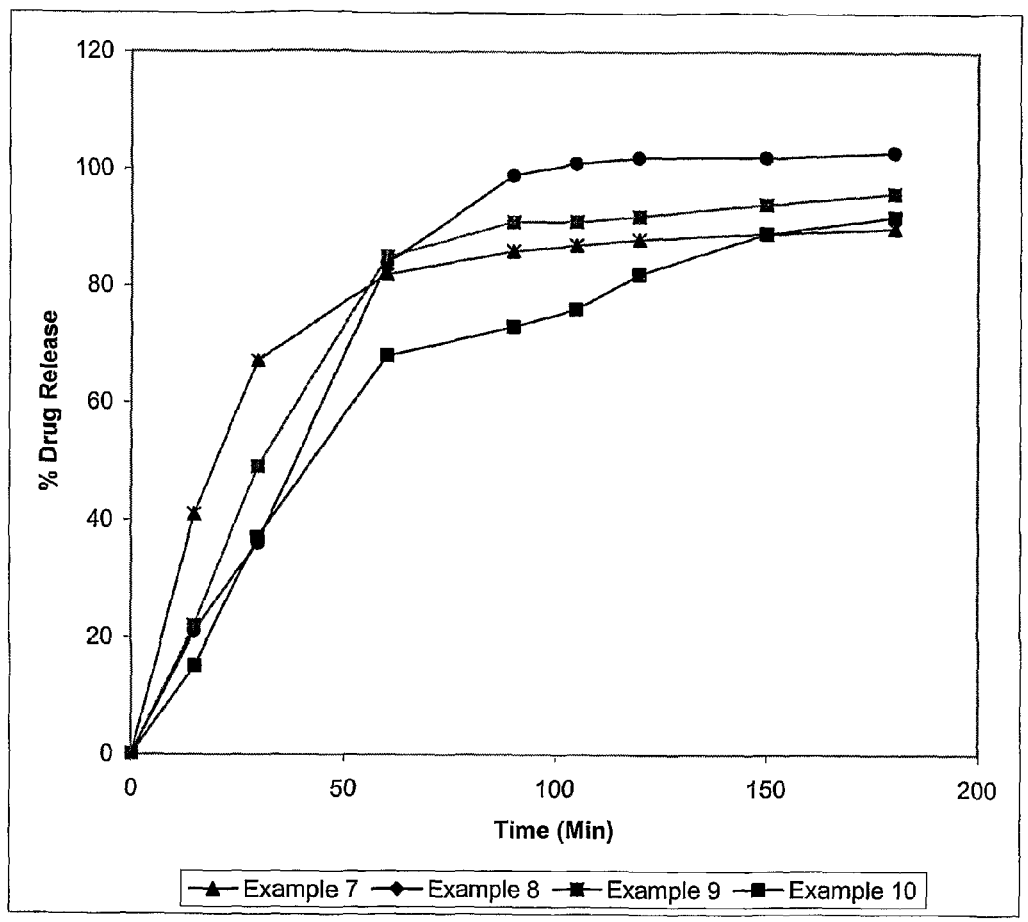

CONTROLLED RELEASE COMPOSITIONS CONTAINING ZOLPIDEM

FIELD OF THE INVENTION

The present invention relates to controlled release compositions of zolpidem or pharmaceutically acceptable salts thereof adapted to release zolpidem over a predetermined time period, according to a monophasic and/or a biphasic profile of dissolution. The present invention also relates to monolithic matrix based formulations of zolpidem or pharmaceutically acceptable salts thereof.

BACKGROUND OF THE INVENTION

Chemically, zolpidem is N,N,6-trimethyl-2-p-tolylimidazo[1,2-a]pyridine-3-acetamide of Formula I. It is commercially available in the form of zolpidem tartrate and marketed as Ambien® and Ambien CR® tablet dosage forms. Zolpidem is a hypnotic agent with a chemical structure unrelated to benzodiazepines, barbiturates, pyrrolopyrazines, pyrazolopyrimidines, or other drugs with known hypnotic properties.

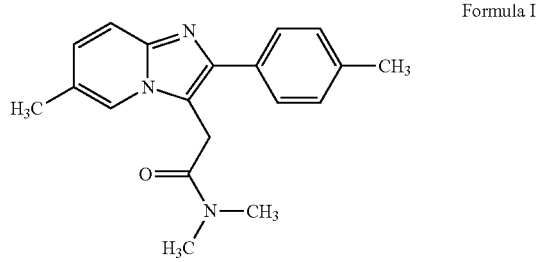

Formula I

In contrast to the benzodiazepines (BZ), which non-selectively bind to and activate all BZ receptor subtypes, zolpidem in vitro binds the $(BZ)_1$ receptor preferentially with a high affinity ratio of the $\alpha_1$-subunits/ $\alpha_5$-subunits. The (BZ), receptor is found primarily on the Lamina IV of the sensorimotor cortical regions, substantia nigra (pars reticulata), cerebellummolecular layer, olfactory bulb, ventral thalamic complex, pons, inferior colliculus, and globus pallidus. This selective binding of zolpidem on the $(BZ)_1$ receptor is not absolute, but it may explain the relative absence of myorelaxant and anticonvulsant effects in animal studies as well as the preservation of deep sleep (stages 3 and 4) in human studies of zolpidem at hypnotic doses.

Pharmacokinetic and pharmacodynamic data show that zolpidem has both a rapid absorption and onset of hypnotic action. Its bioavailability is 70% following oral administration and demonstrates linear kinetics in the therapeutical dose range, which lies between 5 and 10 mg in conventional forms, peak plasma concentration is reached at between 0.5 and 3 hours, the elimination half-life is short, with a mean of 2.4 hours and duration of action of up to 6 hours.

Initially, only immediate release dosage forms of zolpidem were developed, which disintegrate and dissolve rapidly in the gastrointestinal tract and undergo systemic absorption, where zolpidem, can exert its pharmacological effect and induce sleep of the patient. The controlled release dosage forms of zolpidem were developed later, which enable to sustain release of zolpidem over a period compatible with the desired time of sleep and the time needed for elimination of the drug from the human body to a sufficiently low level.

Commercially available controlled release tablets of Ambien CR® consists of a coated two-layer tablet, where one layer releases its drug content immediately and the another layer allows a slower release of additional drug content.

EP 173,928 discloses an oral pharmaceutical controlled release preparation which has a biphasic release profile of a pharmacologically active agent, comprising a core containing the active agent and a coating applied thereon, wherein the coating consists of a film-forming polymer which is insoluble in water and gastro-intestinal fluids and a water-soluble pore-creating material also including the active agent.

EP 361,910 discloses granules, which have a spray-dried substance carrying an adsorbed pharmaceutical and a layer comprising a pharmaceutically acceptable excipient and a pharmaceutical.

GB 2,245,492 discloses an orally administrable programmed release pharmaceutical preparation comprising a core coated with a hydrophobic material and a surfactant.

U.S. Pat. No. 6,514,531 describes controlled release dosage forms adapted to release zolpidem or a salt thereof over a predetermined time period, according to a biphasic in vitro profile of dissolution, where the first phase is an immediate release phase having a maximum duration of 30 minutes and the second phase is a prolonged release phase, and wherein 40 to 70% of the total amount of zolpidem is released during the immediate release phase and the time for release of 90% of the total amount of zolpidem is between 2 and 6 hours.

Several other pharmaceutical compositions containing zolpidem have been reported for example, in U.S. Pat. Nos. 6,638,535; 6,500,459; US Application Nos. 2004258750; 2003165566; 2004185097; 2005008702; and International (PCT) Publication Nos. WO2005115345; WO2006010640; and WO2006008636.

SUMMARY OF THE INVENTION

In one aspect there is provided a pharmaceutical controlled-release dosage form adapted to release zolpidem or a salt thereof over a predetermined time period, according to a monophasic in vitro profile of dissolution.

The controlled-release dosage form may release less than about 40% of the total amount of zolpidem in about 1 to 30 minutes and the time for release of 90% of the total amount of zolpidem is from about 75 to 120 minutes, as measured in a type II dissolution apparatus according to the U.S. Pharmacopoeia in 0.01M hydrochloric acid buffer at 37° C.

The controlled-release dosage form may release from about 40 to about 70% of the total amount of zolpidem in about 1 to 30 minutes and the time for release of 90% of the total amount of zolpidem is from about 75 to 120 minutes, as measured in a type II dissolution apparatus according to the U.S. Pharmacopoeia in 0.01M hydrochloric acid buffer at 37° C.

The controlled-release dosage form may release less than about 40% of the total amount of zolpidem in about 1 to 30 minutes and the time for release of 90% of the total amount of zolpidem is from about 2 to about 6 hours, as measured in a type II dissolution apparatus according to the U.S. Pharmacopoeia in 0.01M hydrochloric acid buffer at 37° C.

The term "total amount of zolpidem" as used herein refers to the quantity by weight of the zolpidem comprised in the whole dosage form.

In another aspect there is provided a pharmaceutical controlled-release dosage form adapted to release zolpidem or a salt thereof over a predetermined time period, according to a biphasic in vitro profile of dissolution.

The controlled-release dosage form may release 40% or less of the total amount of zolpidem in about 1 to 30 minutes as an immediate phase and the time for release of 90% of the total amount of zolpidem is from about 75 to 120 minutes as a prolonged phase, as measured in a type II dissolution apparatus according to the U.S. Pharmacopoeia in 0.01M hydrochloric acid buffer at 37° C.

The controlled-release dosage form may release from about 40 to about 70% of the total amount of zolpidem in about 1 to 30 minutes as an immediate phase and the time for release of 90% of the total amount of zolpidem is from about 75 to 120 minutes as a prolonged release, as measured in a type II dissolution apparatus according to the U.S. Pharmacopoeia in 0.01M hydrochloric acid buffer at 37° C.

The controlled-release dosage form may release less than about 40% of the total amount of zolpidem in about 1 to 30 minutes as an immediate release and the time for release of 90% of the total amount of zolpidem is from about 2 to about 6 hours as a prolonged release, as measured in a type II dissolution apparatus according to the U.S. Pharmacopoeia in 0.01M hydrochloric acid buffer at 37° C.

The controlled-release dosage forms may be in the form of one or more of tablets, capsules, pellets, granules and other dosage forms suitable for administration.

In another general aspect there is provided a pharmaceutical controlled-release dosage form adapted to release zolpidem or a salt thereof over a predetermined time period that includes zolpidem or a salt thereof, hydroxypropylmethyl cellulose and hydroxypropyl cellulose along with one or more other pharmaceutically acceptable excipients.

The one or more pharmaceutically acceptable excipients may include one or more of binders, diluents, and lubricants. The binder may be one or more of polyvinyl pyrrolidone, pregelatinized starch, and gelatin. The diluent may be one or more of lactose, mannitol, and microcrystalline cellulose. The lubricant may be one or more of magnesium stearate, zinc stearate, talc, and colloidal silicon dioxide.

In another general aspect there is provided a pharmaceutical controlled-release monolithic polymeric matrix tablet adapted to release zolpidem or a salt thereof over a predetermined time period, according to an in vitro profile of dissolution when measured in a type II dissolution apparatus according to the U.S. Pharmacopoeia in 0.01M hydrochloric acid buffer at 37° C., wherein 40 to 70% of the total amount of zolpidem is released within 30 minutes and the time for release of 90% of the total amount of zolpidem is between 2 and 6 hours.

The details of one or more embodiments of the inventions are set forth in the description below. Other features, objects and advantages of the inventions will be apparent from the description and claims.

DESCRIPTION OF THE DRAWINGS

FIG. 1 shows a comparative drug release profile of examples 1-3.

FIG. 2 shows a comparative drug release profile of examples 4-6.

FIG. 3 shows a comparative drug release profile of examples 7-10.

DETAILED DESCRIPTION OF THE INVENTION

The inventors have recognized that there is an unmet and unrecognized need for a simpler controlled-release dosage form of zolpidem or salts thereof. In particular, the inventors have now discovered that a controlled-release dosage form of zolpidem or a salt thereof can be effectively made which does not require an immediate release phase and a prolonged release phase for controlling the release of the drug from the dosage form. The release of zolpidem from the dosage form can be controlled according to a monophasic in vitro profile of dissolution. The monophasic system developed for controlled release of zolpidem or salt thereof offers several advantages such as cost, ease of formulation and predictable release profile.

It was also discovered that by changing the composition, the duration of the immediate release phase and prolonged release phases can be significantly altered without affecting the overall dissolution profile.

In addition, it was found that the release of the zolpidem from the dosage form can be controlled from a monolithic matrix. The term "monolithic matrix" as used herein refers to a composition, which does not have immediate and prolonged release phases for controlling the delivery, and the release of the drug from polymer matrix is on a continuous basis.

A first aspect of the present invention provides a pharmaceutical controlled-release dosage form adapted to release zolpidem or a salt thereof over a predetermined time period, according to a monophasic in vitro profile of dissolution when measured in a type II dissolution apparatus according to the U.S. Pharmacopoeia in 0.01M hydrochloric acid buffer at 37° C., wherein less than 40% of the total amount of zolpidem is released between 1 to 30 minutes and the time for release of 90% of the total amount of zolpidem is between 75 to 120 minutes.

The controlled-release dosage form may release from about 40 to about 70% of the total amount of zolpidem in about 1 to 30 minutes and the time for release of 90% of the total amount of zolpidem is from about 75 to 120 minutes, as measured in a type II dissolution apparatus according to the U.S. Pharmacopoeia in 0.01M hydrochloric acid buffer at 37° C.

The controlled-release dosage form may release less than about 40% of the total amount of zolpidem in about 1 to 30 minutes and the time for release of 90% of the total amount of zolpidem is from about 2 to about 6 hours, as measured in a type II dissolution apparatus according to the U.S. Pharmacopoeia in 0.01M hydrochloric acid buffer at 37° C.

The monophasic dissolution profile does not give rise to an immediate release phase followed by a prolonged release phase as the drug is continuously released from the erodible matrix at a constant rate. This type of dissolution aims at achieving an immediate sleep of the patient followed by maintenance of the drug blood level at or below the peak level, but higher than the level obtained with an immediate release dosage form, at the same time after dosing with the objective of maintaining sleep.

The controlled-release dosage form containing zolpidem or a salt thereof adapted for a monophasic dissolution profile includes solid oral dosage forms in the form of one or more of tablets, capsules, pellets, granules and other dosage forms suitable for administration.

The tablet dosage form can be a single or a multi-layer and can be coated or uncoated. Each layer of the tablet can include a functional layer. The tablet dosage form can also include a single functional layer and, optionally, one or more nonfunctional layers adjacent to the single functional layer. Each functional layer may include zolpidem or pharmaceutically acceptable salt and one or more pharmaceutically acceptable rate-controlling polymers.

The functional layer may further include one or more pharmaceutically acceptable excipients. The one or more pharmaceutically acceptable excipients may include one or more of binders, diluents, and lubricants/glidants. The binder may be one or more of polyvinyl pyrrolidone, pregelatinized starch, and gelatin. The diluent may be one or more of lactose, mannitol, and microcrystalline cellulose. The lubricant may be one or more of magnesium stearate, zinc stearate, talc, and colloidal silicon dioxide.

The functional layer may include granules. The one or more nonfunctional layers adjacent to the functional layer may include a cosmetic coating. The cosmetic coating may include a colorant.

The tablets may be prepared by various techniques such as direct compression. Zolpidem or a salt thereof may be blended with one or more pharmaceutically acceptable polymers and one or more pharmaceutically acceptable excipients, which includes a mixture of lactose, tartaric acid and microcrystalline cellulose. This blend is screened and compressed after lubrication.

The tablets may also be prepared by wet granulation or dry granulation. Zolpidem or a salt thereof may be blended with one or more pharmaceutically acceptable polymers and a pharmaceutically acceptable carrier, which includes a mixture of lactose, tartaric acid and microcrystalline cellulose. This blend is then granulated with a suitable binder solution to obtain granules. The granules are further lubricated and compressed.

The tablets may be optionally coated with a nonfunctional layer. The tablet/minitablets may be optionally filled into capsules.

The capsule dosage form can contain a tablet mentioned above placed in empty capsule shell or granules of drug along with one or more rate controlling polymers and excipients can be filled into capsules.

A second aspect of present invention provides a pharmaceutical controlled-release dosage form adapted to release zolpidem or a salt thereof over a predetermined time period, according to a biphasic in vitro profile of dissolution when measured in a type II dissolution apparatus according to the U.S. Pharmacopoeia in 0.01M hydrochloric acid buffer at 37° C., wherein 40% or less of the total amount of zolpidem is released between 1 to 30 minutes as an immediate phase and the time for release of 90% of the total amount of zolpidem is between 75 to 120 minutes as a prolonged phase.

The controlled-release dosage form may release from about 40 to about 70% of the total amount of zolpidem in about 1 to 30 minutes as an immediate phase and the time for release of 90% of the total amount of zolpidem is from about 75 to 120 minutes as a prolonged release, as measured in a type II dissolution apparatus according to the U.S. Pharmacopoeia in 0.01M hydrochloric acid buffer at 37° C.

The controlled-release dosage form may release less than about 40% of the total amount of zolpidem in about 1 to 30 minutes as an immediate release and the time for release of 90% of the total amount of zolpidem is from about 2 to about 6 hours as a prolonged release, as measured in a type II dissolution apparatus according to the U.S. Pharmacopoeia in 0.0 M hydrochloric acid buffer at 37° C.

The first phase or immediate release phase refers to that part of the dissolution profile from 0 to 30 minutes in a suitable in vitro dissolution test. A suitable dissolution test is for example, a method of measurement carried out in a type II dissolution apparatus according to the U.S. Pharmacopoeia in aqueous buffer at 37° C. Other variations of this measurement are well known to a person who is skilled in this art.

The second phase or prolonged release phase is that part of the dissolution profile, which is after 30 minutes, measured in a suitable in vitro dissolution test, as described above. The present invention then proposes dosage forms of the drug whose complete dissolution time for the second phase is either between 75 to 120 minutes or between 2 and 6 hours.

The rapid release in the first phase induces the immediate sleep of the patient and the second phase allows the drug blood level to be maintained at or below the peak level, but higher than the level obtained with an immediate release dosage form, at the same time after dosing with the objective of maintaining sleep.

The present invention also proposes dosage forms of zolpidem or a salt thereof whose complete dissolution time, defined, as the time for release of 90% of the total amount of drug is either between 75 to 105 minutes or between 2 and 6 hours.

Either 25 to 40% or 40 to 70% of the total amount of drug can be released during the immediate release phase.

The controlled release dosage form containing zolpidem or a salt thereof adapted for a biphasic dissolution profile includes solid oral dosage forms in the form of one or more of tablets, capsules, pellets, granules and other dosage forms suitable for administration.

The tablet dosage form can be a single or a multi-layer and can be coated or uncoated. Each layer of the tablet can include a functional layer. The tablet dosage form can also include a single functional layer and, optionally, one or more nonfunctional layers adjacent to the single functional layer. The tablet can contain an immediate release portion of the drug mixed with a prolonged release coated pellets of the drug. Each functional layer may include zolpidem or pharmaceutically acceptable salt and one or more pharmaceutically acceptable rate-controlling polymers.

The functional layer may further include one or more pharmaceutically acceptable excipients. The one or more pharmaceutically acceptable excipients may include one or more of binders, diluents, and lubricants/glidants. The binder may be one or more of polyvinyl pyrrolidone, pregelatinized starch, and gelatin. The diluent may be one or more of lactose, mannitol, and microcrystalline cellulose. The lubricant may be one or more of magnesium stearate, zinc stearate, talc, and colloidal silicon dioxide.

The functional layer may include granules. The one or more nonfunctional layers adjacent to the functional layer may include a cosmetic coating. The cosmetic coating may include a colorant.

The tablets may be prepared by direct compression. The immediate release and the prolonged release granules can be separately prepared, blended and compressed using suitable tooling to get a single layer tablet. Alternatively, the immediate release granules can be compressed along with prolonged release granules to get a bi-layered tablet.

For making immediate release granules, zolpidem or a salt thereof is mixed with suitable pharmaceutically acceptable excipients as provided herein and the blend is lubricated and compressed.

For making prolonged release granules, zolpidem or a salt thereof may be blended with one or more pharmaceutically acceptable polymers and one or more pharmaceutically acceptable excipients, which includes a mixture of lactose, tartaric acid and microcrystalline cellulose. This blend is screened and compressed after lubrication.

The tablets may also be prepared by wet granulation or dry granulation. Zolpidem or a salt thereof may be blended with one or more pharmaceutically acceptable polymers and a pharmaceutically acceptable carrier, which includes a mixture of lactose, tartaric acid and microcrystalline cellulose. This blend is then granulated with a suitable binder solution to obtain granules. The granules are further lubricated and compressed to get desired single layer or bi-layered tablet comprising individual layers of immediate release and prolonged release.

The immediate and prolonged released granules can be filled into empty capsule shells or individual tablet of either immediate release granules or prolonged release granules or vice versa can be placed into empty capsule shells.

A third aspect of the present invention provides a pharmaceutical controlled-release dosage form adapted to release zolpidem or a salt thereof over a predetermined time period, comprising zolpidem or a salt thereof, hydroxypropylmethyl cellulose and hydroxypropyl cellulose.

The controlled release dosage form may further include one or more pharmaceutically acceptable excipients. The one or more pharmaceutically acceptable excipients may include one or more of binders, diluents, and lubricants/glidants. The binder may be one or more of polyvinyl pyrrolidone, pregelatinized starch, and gelatin. The diluent may be one or more of lactose, mannitol, and microcrystalline cellulose. The lubricant may be one or more of magnesium stearate, zinc stearate, talc, and colloidal silicon dioxide.

A fourth aspect of the present invention provides a pharmaceutical controlled-release monolithic polymeric matrix tablet adapted to release zolpidem or a salt thereof over a predetermined time period, according to an in vitro profile of dissolution when measured in a type II dissolution apparatus according to the U.S. Pharmacopoeia in 0.01M hydrochloric acid buffer at 37° C., wherein 40 to 70% of the total amount of zolpidem is released within 30 minutes and the time for release of 90% of the total amount of zolpidem is between 2 and 6 hours.

The controlled release dosage form containing zolpidem or a salt thereof embedded in a monolithic polymer matrix includes solid oral dosage forms in the form of one or more of tablets, capsules, pellets, granules and other dosage forms suitable for administration.

The tablet can be coated or uncoated. The tablets include zolpidem or pharmaceutically acceptable salt and one or more pharmaceutically acceptable rate-controlling polymers.

The tablet may further include one or more pharmaceutically acceptable excipients. The one or more pharmaceutically acceptable excipients may include one or more of binders, diluents, and lubricants/glidants. The binder may be one or more of polyvinyl pyrrolidone, pregelatinized starch, and gelatin. The diluent may be one or more of lactose, mannitol, and microcrystalline cellulose. The lubricant may be one or more of magnesium stearate, zinc stearate, talc, and colloidal silicon dioxide.

The tablets may be prepared by direct compression. Zolpidem or a salt thereof may be blended with one or more pharmaceutically acceptable polymers and one or more pharmaceutically acceptable excipients, which includes a mixture of lactose, tartaric acid and microcrystalline cellulose. This blend is screened and compressed after lubrication.

The tablets may also be prepared by wet granulation or dry granulation. Zolpidem or a salt thereof may be blended with one or more pharmaceutically acceptable polymers and a pharmaceutically acceptable carrier, which includes a mixture of lactose, tartaric acid and microcrystalline cellulose. This blend is then granulated with a suitable binder solution to obtain granules. The granules are further lubricated and compressed.

The tablets may be optionally coated with a nonfunctional layer. The tablet/minitablets may be optionally filled into capsules.

The capsule dosage form can contain a tablet mentioned above placed in empty capsule shell or granules of drug along with one or more rate controlling polymers and excipients can be filled into capsules.

The pharmaceutically acceptable rate controlling polymers may be one or more of carbohydrate gum, polyuronic acid salts, cellulose ethers, acrylic acid polymers, and mixtures thereof.

Suitable carbohydrate gums include one or more of xanthan gum, tragacanth gum, gum karaya, guar gum, acacia, gellan, locust bean gum and other carbohydrate gums having similar properties.

Suitable polyuronic acid salts include one or more of alkali metal salts of alginic acid or pectic acid and mixtures thereof. Suitable alkali metal salts of alginic acid that may be used include one or more of sodium alginate, potassium alginate, ammonium alginate and other suitable alkali metal salts of alginic acid.

Suitable cellulose ethers include one or more of hydroxypropyl methylcellulose, hydroxypropyl cellulose and other suitable cellulose ethers. The combination of hydroxypropyl methylcellulose, hydroxypropyl cellulose provides unique characteristic in terms of controlling the release in the required manner.

Suitable acrylic acid polymers include any suitable polyacrylic acid polymers or carboxyvinyl polymers such as those available under the brand name carbopol.

Pharmaceutically acceptable excipients can be diluent, filler, binder, lubricant, sweetener, coloring and flavoring agent, glidant, and the like. The binders may be one or more of starch, sugars, gums, low molecular weight hydroxypropyl methylcellulose, polyvinyl pyrrolidone and hydroxypropyl cellulose. The lubricants may be one or more of talc, magnesium stearate, calcium stearate, polyethylene glycol, hydrogenated vegetable oils, stearic acid, sodium stearyl fumarate and sodium benzoate. The glidants may be one or both of colloidal silicon dioxide and talc. Suitable coloring or flavoring agents include those approved for use by the United States Food and Drug Administration (FDA) and are well known to those skilled in the art.

The present invention is further illustrated by the following examples which are provided merely to be exemplary of the invention and do not limit the scope of the invention. Certain modifications and equivalents will be apparent to those skilled in the art and are intended to be included within the scope of the present invention.

EXAMPLE 1 TO 3

The composition of three batches is provided in Table 1.

Zolpidem tartrate, tartaric acid, lactose, HPMC, microcrystalline cellulose and HPC were passed through ASTM mesh #30 and mixed in suitable blender. Lubricant was passed through ASTM mesh #40 and mixed with the earlier blend. The total blend was compressed using suitable tooling.

Table 2 provides the dissolution data of the tablets prepared as per the Formula provided in Table 1. For determination of drug release rate, 0.01M hydrochloric acid buffer in 900 ml of medium using USP Type 2 Apparatus (rpm 50) was used.

TABLE 1

| S.N. | Ingredients | Qty/Tablet [mg] Example 1 | Qty/Tablet [mg] Example 2 | Qty/Tablet [mg] Example 3 |
|---|---|---|---|---|
| 1 | Zolpidem Tartrate | 12.5 | 12.5 | 12.5 |
| 2 | Tartaric acid | 2.5 | 2.5 | 2.5 |

TABLE 1-continued

| S.N. | Ingredients | Qty/Tablet [mg] Example 1 | Qty/Tablet [mg] Example 2 | Qty/Tablet [mg] Example 3 |
|---|---|---|---|---|
| 3 | Lactose Monohydrate | 73.5 | 43.5 | 96.0 |
| 4 | Hydroxypropyl cellulose [HPC-L] | 45.0 | 65.0 | 37.5 |
| 5 | Hydroxypropyl cellulose [HPC-M] | — | — | — |
| 5 | Methocel E-5 | 45.0 | 65.0 | — |
| 6 | Methocel E-15 | — | — | 30.0 |
| 7 | Microcrystalline Cellulose | 69.0 | 69.0 | 69.0 |
| 8 | Magnesium Stearate | 2.5 | 2.5 | 2.5 |
|  | Total Wt. | 250.0 | 250.0 | 250.0 |

TABLE 2

Dissolution data

| Time [min] | % Drug released Example 1 | % Drug released Example 2 | % Drug released Example 3 |
|---|---|---|---|
| 0 | 0 | 0 | 0 |
| 15 | 17 | 18 | 20 |
| 30 | 37 | 33 | 50 |
| 60 | 77 | 78 | 86 |
| 90 | 89 | 86 | 95 |
| 105 | 92 | 87 | 97 |
| 120 | 94 | 87 | 98 |
| 150 | 96 | 88 | 99 |
| 180 | 97 | 89 | 100 |

EXAMPLE 4 TO 6

The composition of three batches is provided in Table 3.
Table 4 provides the dissolution data of the tablets prepared as per the Formula provided in Table 3. For determination of drug release rate, 0.01M hydrochloric acid buffer in 900 ml of medium using USP Type 2 Apparatus (rpm 50) was used.

TABLE 3

| S. No | Ingredients | Qty/Tablet [mg] Example 4 | Qty/Tablet [mg] Example 5 | Qty/Tablet [mg] Example 6 |
|---|---|---|---|---|
|  | IR Layer |  |  |  |
| 1 | Zolpidem Tartrate | 1.50 | 2.00 | 1.50 |
| 2 | Lactose Monohydrate | 72.40 | 71.90 | 72.40 |
| 3 | Microcrystalline Cellulose | 20.00 | 20.00 | 20.00 |
| 4 | Plasdone S 630 | 2.00 | 2.00 | 2.00 |
| 5 | Ac-di-sol | 3.00 | 3.00 | 3.00 |
| 6 | Yellow Iron Oxide | 0.10 | 0.10 | 0.10 |
| 7 | Magnesium Stearate | 1.00 | 1.00 | 1.00 |
|  | ER Layer |  |  |  |
| 1 | Zolpidem Tartrate | 11.00 | 10.50 | 11.00 |
| 2 | Lactose Monohydrate | 52.00 | 52.50 | 88.00 |
| 3 | Microcrystalline Cellulose | 55.00 | 55.00 | 55.00 |
| 4 | Hydroxypropyl cellulose [HPC-L] | 60.00 | 60.00 | 24.00 |
| 5 | Methocel K 100 LV CR | 20.00 | 20.00 | — |
| 6 | Methocel E 5 | — | — | 20.00 |
| 7 | Magnesium Stearate | 2.00 | 2.00 | 2.00 |
|  | Total Wt. | 300.00 | 300.00 | 300.00 |

Brief Procedure:

Immediate Release Granules: Zolpidem tartrate, lactose, microcrystalline cellulose, plasdone S630, croscarmellose sodium and yellow iron oxide were passed through ASTM mesh #40 and mixed in suitable blender. Lubricant was passed through ASTM mesh #40 and mixed with the earlier blend.

Prolonged Release Granules: Zolpidem tartrate, lactose, HPMC, microcrystalline cellulose and SPC were passed through ASTM mesh #30 and mixed in suitable blender. Lubricant was passed through ASTM mesh #40 and mixed with the earlier blend.

IR and ER layers were compressed as a single or a bi-layered tablet using suitable tooling.

TABLE 4

Drug Release data

| Time [min] | % Drug released Example 4 | % Drug released Example 5 | % Drug released Example 6 |
|---|---|---|---|
| 0 | 0 | 0 | 0 |
| 15 | 22 | 26 | 35 |
| 30 | 31 | 37 | 58 |
| 60 | 45 | 47 | 82 |
| 90 | 57 | 59 | 91 |
| 105 | 63 | 64 | 95 |
| 120 | 68 | 70 | 98 |
| 180 | 84 | 87 | 99 |
| 240 | 93 | 96 | 99 |

EXAMPLE 7 TO 10

The composition of four batches is provided in Table 5. Varying percentages of HPMC and HPC were used as rate controlling polymers.

Zolpidem tartrate, tartaric acid, lactose, HPMC, microcrystalline cellulose and HPC were passed through ASTM mesh #30 and mixed in suitable blender. Lubricant was passed through ASTM mesh #40 and mixed with the earlier blend. The total blend was compressed using suitable tooling.

Table 6 provides the dissolution data of the tablets prepared as per the Formula provided in Table 5. For determination of drug release rate, 0.01M hydrochloric acid buffer in 900 ml of medium using USP Type 2 Apparatus (rpm 50) was used.

TABLE 5

| S. No | Ingredients | Qty/Tablet [mg] Example 7 | Qty/Tablet [mg] Example 8 | Qty/Tablet [mg] Example 9 | Qty/Tablet [mg] Example 10 |
|---|---|---|---|---|---|
| 1 | Zolpidem Tartrate | 12.5 | 12.5 | 12.5 | 12.5 |
| 2 | Tartaric acid | 2.5 | — | 2.5 | 2.5 |
| 3 | Lactose Monohydrate | 103.5 | 93.5 | 88.5 | 63.5 |
| 4 | Hydroxypropyl cellulose [HPC-L] | 30.0 | 37.5 | — | 50.0 |
| 5 | Hydroxypropyl cellulose [HPC-M] | — | 5.0 | 37.5 | — |
| 5 | Methocel E-5 | — | 30.0 | 37.5 | 50.0 |
| 6 | Methocel E-15 | 30.0 | — | | |
| 7 | Microcrystalline Cellulose | 69.0 | 69.0 | 69.0 | 69.0 |
| 8 | Magnesium Stearate | 2.5 | 2.5 | 2.5 | 2.5 |
|  | Total Wt. | 250.0 | 250.0 | 250.0 | 250.0 |

TABLE 6

| | Dissolution data | | | |
|---|---|---|---|---|
| Time [min] | % Drug released Example 7 | % Drug released Example 8 | % Drug released Example 9 | % Drug released Example 10 |
| 0 | 0 | 0 | 0 | 0 |
| 15 | 41 | 21 | 22 | 15 |
| 30 | 67 | 36 | 49 | 37 |
| 60 | 82 | 84 | 85 | 68 |
| 90 | 86 | 99 | 91 | 73 |
| 105 | 87 | 101 | 91 | 76 |
| 120 | 88 | 102 | 92 | 82 |
| 150 | 89 | 102 | 94 | 89 |
| 180 | 90 | 103 | 96 | 92 |

While the present invention has been described in terms of its specific embodiments, certain modifications and equivalents will be apparent to those skilled in the art and are intended to be included within the scope of the present invention.

We claimed:

1. A dry granulated pharmaceutical dosage form comprising a polymer matrix, wherein said polymer matrix comprises zolpidem or a pharmaceutically acceptable salt thereof, one or more rate controlling polymers, and one or more pharmaceutically acceptable excipients, wherein the dosage form is adapted to release zolpidem or a salt thereof on a continuous basis over a predetermined time period, according to an in vitro profile of dissolution when measured in a type II dissolution apparatus according to U.S. Pharmacopoeia in 0.01 M hydrochloric acid buffer at 37° C. , wherein less than 40% of the total amount of zolpidem is released between 15 to 30 minutes and the time for release of 90% of the total amount of zolpidem is between 2 to 6 hours; and wherein the dosages form is a controlled release pharmaceutical composition.

2. The pharmaceutical-controlled release dosage form of claim 1, wherein the release rate-controlling polymers comprises one or more of carbohydrate gum, polyuronic acid salts, cellulose ethers and acrylic acid polymers.

3. The pharmaceutical controlled-release dosage form of claim 2, wherein the release rate-controlling polymers are cellulose ethers.

4. The pharmaceutical controlled-release dosage form of claim 3, wherein the cellulose ethers comprises one or more of hydroxypropylmethyl cellulose and hydroxypropyl cellulose.

5. The pharmaceutical controlled-release dosage form of claim 1, wherein the dosage form comprises one or more of tablets, capsules, pellets and granules.

6. A pharmaceutical controlled-release dosage form according to claim 1 in the form of a monolithic polymeric matrix dosages form.

7. The pharmaceutical controlled-release dosage form of claim 6 further comprises of one or more release rate-controlling polymers.

8. The pharmaceutical-controlled release dosage form of claim 7, wherein the release rate-controlling polymers comprises one or more of carbohydrate gum, polyuronic acid salts, cellulose ethers and acrylic acid polymers.

9. The pharmaceutical controlled-release dosages form of claim 8, wherein the release rate-controlling polymers are cellulose ethers.

10. A pharmaceutical controlled-release dosage form adapted to release zolpidem or a pharmaceutically acceptable salt thereof over a predetermined time period, according to an in vitro profile of dissolution when measured in a type II dissolution apparatus according to U.S. Pharmacopoeia in 0.01M hydrochloric acid buffer at 37° C, the dosage form comprising 5% zolpidem tartrate, 1% tartaric acid, 41.4% lactose monohydrate, 12% hydroxyl propyl cellulose, 12% Methocel E-15, 27.6% microcrystalline cellulose and 1% magnesium stearate, wherein the blend is compressed; and wherein 67% of the total amount of zolpidem is released within the first 30 minutes, 88% of the total amount of zolpidem is released within the first 120 minutes, and 90% of the total amount of zolpidem is released within the first 180 minutes.

* * * * *